United States Patent [19]

Blankley et al.

[11] 4,271,164

[45] Jun. 2, 1981

[54] 6-SUBSTITUTED-ARYLPYRIDO[2,3-d]PYRIMIDIN-7-AMINES AND DERIVATIVES

[75] Inventors: Clifton J. Blankley, Ann Arbor; Lawrence R. Bennett, Chelsea, both of Mich.

[73] Assignee: Warner-Lambert Company, Morris Plains, N.J.

[21] Appl. No.: 123,781

[22] Filed: Mar. 11, 1980

Related U.S. Application Data

[63] Continuation-in-part of Ser. No. 30,195, Apr. 16, 1979, abandoned.

[51] Int. Cl.³ .................. C07D 471/04; A61K 31/495
[52] U.S. Cl. .................................... 424/251; 544/279; 544/326; 544/329; 548/336
[58] Field of Search .................... 544/279; 424/251

[56] References Cited

U.S. PATENT DOCUMENTS

| 3,534,039 | 11/1970 | Davoll | 544/279 |
| 3,639,401 | 2/1972 | Meyer | 424/251 |

FOREIGN PATENT DOCUMENTS

| 796753 | 10/1968 | Canada | 544/279 |
| 4377M | 10/1966 | France . | |
| 1129084 | 10/1968 | United Kingdom . | |
| 1171218 | 11/1969 | United Kingdom | 544/279 |

OTHER PUBLICATIONS

Hulbert et al., "Journ. Med. Chem.," vol. 11, 1968, pp. 703–717.

*Primary Examiner*—Donald G. Daus
*Assistant Examiner*—James H. Turnipseed
*Attorney, Agent, or Firm*—Walter Patton

[57] ABSTRACT

6-Substituted-arylpyrido[2,3-d]pyrimidin-7-amines and derivatives and their pharmaceutically acceptable acid addition salts are useful in the treatment of hypertension.

24 Claims, No Drawings

6-SUBSTITUTED-ARYLPYRIDO[2,3-d]PYRIMIDIN-7-AMINES AND DERIVATIVES

CROSS-REFERENCE TO RELATED APPLICATION

This is a continuation-in-part of copending application U.S. Ser. No. 30,195, filed Apr. 16, 1979, now abandoned.

BACKGROUND OF THE INVENTION

This invention relates to 6-substituted-arylpyrido[2,3-d]pyrimidin-7-amines and derivatives thereof which are useful in the treatment of hypertension.

U.S. Pat. No. 3,543,039 to Davoll, issued Oct. 13, 1970, discloses 2,7-diamino-6-arylpyrido[2,3-d]pyrimidine compounds which possess diuretic activity. This patent also discloses 2-substituted-7-amino-6-arylpyrido[2,3-d]pyrimidine compounds as precursors for the aforementioned compounds, where the 2-substituent group is halogen, lower alkoxy, or lower alkylthio.

U.S. Pat. No. 3,639,401 to Meyer, issued Feb. 1, 1972, discloses 6-aryl-2,7-bis-[(trialkylsilyl)amino]pyrido[2,3-d]pyrimidines which are also useful as diuretic agents. British Pat. No. 1,129,084, published Oct. 2, 1968, discloses 2,4,7-triaminopyrido[2,3-d]pyrimidines which can be used to treat bacterial infections and additionally possessing diuretic activity. These latter compounds can be prepared from 7-chloro-2,4-diaminopyrido[2,3-d]-pyrimidines. Hurlbert, et al., in J. Med. Chem., 11, (1968) at pages 703–710 discloses the synthesis of 2,4-diaminopyrido[2,3-d]pyrimidines from beta-keto esters and at pages 711–717 discloses the antimicrobial properties of certain derivatives of 2,4-diaminopyrido[2,3-d]pyrimidines.

SUMMARY OF THE INVENTION

It has now been found that 6-substituted-arylpyrido[2,3-d]pyrimidin-7-amines and their derivatives having the following structural formula:

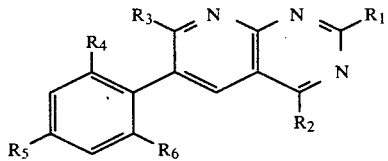

and their pharmaceutically acceptable acid addition salts are useful as antihypertensive agents; wherein $R_1$ and $R_2$ are hydrogen or alkyl; $R_4$ is halogen or alkyl; $R_5$ and $R_6$ are hydrogen, halogen or alkyl; $R_3$ is

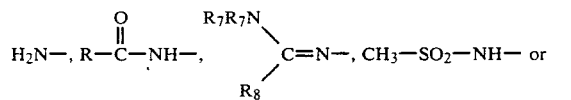

R is hydrogen, alkyl, haloalkyl, alkoxy, alkoxymethylene, mono- or dialkylamino, trifluoromethyl, furyl, pyridyl or phenyl; $R_7$ is hydrogen or alkyl; and $R_8$ is hydrogen or alkylamino; with the provisos that (1) when $R_3$ is $H_2N$—; $R_2$, $R_5$ and $R_6$ are hydrogen and (a) $R_1$ is hydrogen, $R_4$ is not chlorine; (b) $R_1$ is methyl, $R_4$ is not fluoro, iodo or ethyl; and (c) $R_1$ is ethyl, $R_4$ is not chloro or methyl; and (2) when $R_8$ is hydrogen, $R_7$ is not hydrogen.

The term "alkoxy" and "alkoxy" as used herein include radicals containing 1 to 3 carbon atoms.

Preferred compounds of the present invention are those with a 7-amino group having the structural formula:

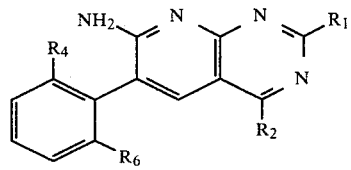

and the non-toxic, pharmaceutically acceptable salts thereof; wherein $R_1$ and $R_2$ are hydrogen or methyl; $R_4$ is halogen, methyl or ethyl; and $R_6$ is hydrogen, chlorine, bromine or methyl; with the provisos that when $R_2$ and $R_6$ are hydrogen and (a) $R_1$ is hydrogen, $R_4$ is not chlorine; (b) $R_1$ is methyl, $R_4$ is not fluoro, iodo or ethyl; and (c) $R_1$ is ethyl, $R_4$ is not chloro or methyl.

Another preferred group of compounds of the invention are those wherein $R_3$ is

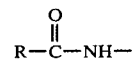

having the structural formula:

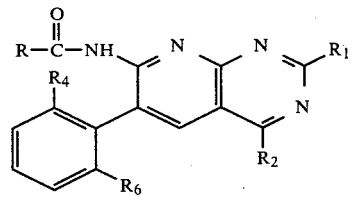

and non-toxic, pharmaceutically acceptable acid addition salts thereof; wherein $R_1$ and $R_2$ are hydrogen or methyl; $R_4$ is halogen, methyl or ethyl; $R_6$ is hydrogen, chlorine, bromine or methyl; and R is hydrogen, methyl, ethyl, chloromethyl, methoxy, methoxymethylene, methyl- and dimethylamino, trifluoromethyl, 2-furyl, 2- and 3-pyridyl, or phenyl.

Still further preferred compounds of the invention are:

6-(2,6-dichlorophenyl)-2-methylpyrido[2,3-d]-pyrimidin-7-amine;
6-(2,6-dichlorophenyl)pyrido[2,3-d]pyrimidin-7-amine;
6-(2-methylphenyl)pyrido[2,3-d]pyrimidin-7-amine;
N-[6-(2,6-dichlorophenyl)-2-methylpyrido[2,3-d]-pyrimidin-7-yl]acetamide;
6-(2-bromo-6-chlorophenyl)-2-methylpyrido[2,3-d]-pyrimidin-7-amine;
6-(2-bromo-6-chlorophenyl)pyrido[2,3-d]pyrimidin-7-amine;
6-(2,6-dichlorophenyl)-4-methylpyrido[2,3-d]-pyrimidin-7-amine;
6-(2,6-dichlorophenyl)-2,4-dimethylpyrido[2,3-d]-pyrimidin-7-amine;
6-(2,6-dibromophenyl)-2-methylpyrido[2,3-d]-pyrimidin-7-amine;

N-[6-(2,6-dichlorophenyl)-2-methylpyrido[2,3-d]-pyrimidin-7-yl]propanamide;

N-[6-(2,6-dichlorophenyl)-2-methylpyrido[2,3-d]-pyrimidin-7-yl]-2-furancarboxamide;

N-[6-(2,6-dichlorophenyl)-2-methylpyrido[2,3-d]-pyrimidin-7-yl]-2-pyridinecarboxamide;

N-[6-(2,6-dichlorophenyl)-2-methylpyrido[2,3-d]-pyrimidin-7-yl]-3-pyridinecarboxamide;

N-[6-(2,6-dichlorophenyl)-2-methylpyrido[2,3-d]-pyrimidin-7-yl]-2-methoxyacetamide;

2-chloro-N-[6-(2,6-dichlorophenyl)-2-methyl-pyrido[2,3-d]pyrimidin-7-yl]acetamide;

N-[6-(2,6-dichlorophenyl)-2-methylpyrido[2,3-d]-pyrimidin-7-yl]carbamic acid, methyl ester; and N-[6-(2,6-dichlorophenyl)-2-methylpyrido[2,3-d]-pyrimidin-7-yl]benzamide.

The invention is also directed to novel methods of synthesizing said compounds and the non-toxic, pharmaceutically acceptable acid addition salts thereof. Additionally, the present invention is directed to pharmaceutical compositions for treating hypertension in mammals comprising an effective amount of said compound or the non-toxic, pharmaceutically acceptable salts thereof together with an inert pharmaceutical carrier. "Effective amount" means an amount sufficient to bring about the desired antihypertensive effect. The present invention is also directed to a method of treating hypertension in mammals by administering an effective amount of said compounds or the non-toxic, pharmaceutically acceptable acid addition salts thereof.

DESCRIPTION OF PREFERRED EMBODIMENTS

The compounds of the invention wherein $R_3$ is —$NH_2$ which have the formula,

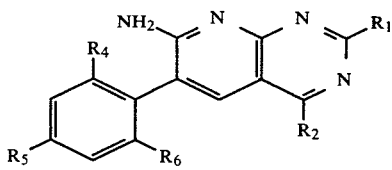

can be produced by reacting a phenylacetonitrile of formula,

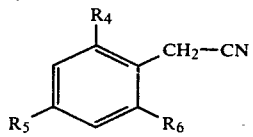

with a 4-aminopyrimidine-5-carboxaldehyde compound of formula,

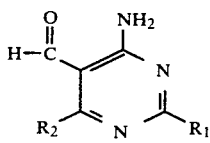

in the presence of a basic catalyst; where $R_1$, $R_2$, $R_4$, $R_5$ and $R_6$ have the same meaning as previously defined. Suitable basic catalysts are alkali metal hydroxides, alkoxides, amides and hydrides. The reaction is preferably carried out in an organic solvent which optionally may contain water, using approximately equivalent amounts of the phenylacetonitrile compound and 4-aminopyrimidine-5-carboxaldehyde compound. If desired, up to about a 50% excess of either of the reactants may be used. Suitable organic solvents are alkanols, alkoxyalkanols, tertiary amides, and dimethylsulfoxide.

The reaction may be carried at a temperature between about 25° C. and 150° C. At least two hours should be allowed for completion of the reaction and preferably from three to forty-eight hours depending on the temperature used. At about 80° C. the reaction is usually complete in three to six hours, especially when using sodium methoxide or ethoxide as the catalyst and carrying out the reaction in ethanol or 2-ethoxyethanol.

The 4-aminopyrimidine-5-carboxaldehyde compounds used as starting materials can be prepared by catalytic reduction of the corresponding 4-aminopyrimidine-5-carbonitriles which in turn may be prepared by the methods described in J. Chem. Soc. 386 (1943); Zeit. Physiol. Chem 242, 89 (1939); J. Am. Chem. Soc., 82, 5711 (1960); and Ber. 71, 87 (1938). Phenylacetonitrile compounds used as starting materials are either known or readily available by application of the published procedures used for the preparation of the known compounds of this type.

The compounds of the invention wherein $R_3$ is other than —$NH_2$ can be produced in various ways from the compounds of the invention wherein $R_3$ is —$NH_2$.

The compounds of the invention wherein $R_3$ is

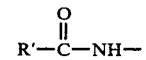

(R' being hydrogen, haloalkyl, alkoxy, alkoxymethylene, trifluoromethyl, furyl, pyridyl or phenyl) can be prepared by reacting a compound of the invention wherein $R_3$ is —$NH_2$ with an acylating agent of formula, R'COY, where Y is a standard leaving group of an acylating agent. Suitable acylating agents include symmetrical anhydrides, acyl halides, acyl imidazolides, and mixed anhydrides with formic acid or carbonic acid esters. The reaction is preferably carried out by reacting the 6-aryl-pyrido[2,3-d]-pyrimidin-7-amine compound with from 1 to 20 equivalents of the acylating agent either in an excess of the acylating agent or a non-protic solvent such as an ester of a lower fatty acid, ether, tetrahydrofuran, chlorinated hydrocarbons, and aromatic hydrocarbons. Preferred solvents are an excess of the acylating agent, ethyl acetate, tetrahydrofuran, 1,2-dichloroethane and toluene. The reaction is carried out at a temperature between about 25° C. and about 120° C. for slightly more than one hour, preferably for about 1.5 to about 24 hours. At 95° C. the reaction is usually complete within about 1.5 to about 5 hours.

The compounds of the invention wherein $R_3$ is a —NHCO—NH—alkyl or —NHCS—NH—$CH_3$ group can be prepared by reacting a compound of the invention wherein $R_3$ is —$NH_2$ with an alkyl isocyanate (alkyl—NCO) or methyl isothiocyanate ($CH_3$—NCS), respectively. As solvents for the reaction ethers, tetrahydrofuran, chlorinated hydrocarbons, aromatic hydrocarbons or an excess of the alkyl isocyanate or methyl isothiocyanate may be used. Generally, the alkyl isocyanate or methyl isothiocyanate is used in about a 1.5 to 20 molar excess and the reaction carried out at a temperature of about 25° C. to 120° C. The reaction in the case of the alkyl isocyanates is usually complete in about 1 to 10 hours, and in the case of the methyl isothiocyanates in about 10 to 50 hours.

The compounds of the invention wherein $R_3$ is —NH—CO—NH$_2$, —NH—CO—NH-alkyl, —NH—CO—N=(alkyl)$_2$ or —NH—CO—O-alkyl can be prepared by first reacting a compound of the invention wherein $R_3$ is —NH$_2$ with carbonyldiimidazole and then reacting the resulting intermediate with ammonia, an alkylamine, a dialkylamine or an alkanol, respectively. In this two-step reaction, the compound of the invention wherein $R_3$ is NH$_2$ is initially reacted with the carbonyldiimidazole in a non-protic solvent such as ether, tetrahydrofuran, a chlorinated hydrocarbon or an aromatic hydrocarbon. Generally about one to about two moles of carbonyldiimidazole per mole of the compound of the invention wherein $R_3$ is NH$_2$— are employed. The reaction medium is heated for at least about one hour, preferably from about five to about forty-eight hours up to about the reflux temperature of the particular solvent.

In the second step of this two-step reaction, the appropriate alcohol or amine is added to the reaction medium in an amount of about two to about five moles of alcohol (alkyl—OH) per mole of compound of the invention wherein $R_3$ is NH$_2$— and about equimolar ratios of ammonia, primary amine, or secondary amine ($R_7R_7$NH) to the compound of the invention wherein $R_3$ is NH$_2$—. When ammonia, primary amine, or secondary amine is added to the reaction medium in the form of a salt in a tertiary amine base, the appropriate ratios are about two to about five equivalents of amine salt in a tertiary amine base to the compound of the invention wherein $R_3$ is NH$_2$—. The amine salts are in approximately equivalent amount to the tertiary amine base.

The reaction medium in the second step is heated, preferably to a temperature between about 25° C. and about 80° C., for at least about one-half hour, preferably from about one-half hour to about two hours.

The compounds of the invention wherein $R_3$ is —NHSO$_2$CH$_3$ can be prepared by reacting a compound of the invention wherein $R_3$ is —NH$_2$ with methanesulfonyl anhydride or a methanesulfonyl halide in the presence of a tertiary amine.

Suitable tertiary amine bases include trialkyl amines and substituted pyridines. The ratio of reactants is about 1.2 to about 1.5 moles of methanesulfonyl anhydride [(CH$_3$SO$_2$)$_2$O]/methanesulfonyl halide (CH$_3$SO$_2$D) per mole of compound of the invention wherein $R_3$ is NH$_2$— and about 0.9 to about 1.0 mole of tertiary amine base per mole of methanesulfonyl anhydride [(CH$_3$SO$_2$)$_2$O]/methanesulfonyl halide (CH$_3$SO$_2$D) wherein D represents a halide.

Suitable solvents for this reaction an non-protic solvents such as ether, tetrahydrofuran, chlorinated hydrocarbons and aromatic hydrocarbons. The reaction medium is heated to a temperature between about 0° C. and about 50° C., for at least about one-half hour.

The compounds of the invention wherein $R_3$ is —N=CH—N=(alkyl)$_2$ can be prepared by reacting a compound of the invention wherein $R_3$ is —NH$_2$ with a N,N—dialkylformamide dialkylacetal or with the addition complex of a N,N-dialkylformamide and a hydrohalogenating agent, (alkyl)$_2$=N$^+$=CHX B$^-$ (where X is halogen and B is the associated anion) to form the corresponding N'-[6-arylpyrido[2,3-d]pyrimidin-7-yl]-N,N-methanimidamide. Suitable hydrohalogenating agents for forming addition complexes with N,N-dialkylformamides are selected from the group consisting of phosgene, thionyl chloride and phosphorous oxyhalides. Generally, the N,N-dialkylformamide dialkylacetals or addition complex of N,N-dialkylformamide and hydrohalogenating agent are used in about 1.5 to about 20 molar excess over the compound of the invention wherein $R_3$ is NH$_2$—. The reaction may be run in a non-protic solvent such as ether, tetrahydrofuran, a chlorinated hydrocarbon, an aromatic hydrocarbon or excess amide acetal. Excess amide acetal is the preferred solvent.

The reaction mixture is heated, preferably to a temperature between about 25° C. and about 120° C., for at least about one-half hour, preferably from about one-half hour to about 12 hours.

The compounds of the invention wherein $R_3$ is

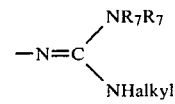

can be prepared by reacting a compound of the invention wherein $R_3$ is

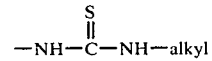

with ammonia, an alkylamine or a dialkylamine in the presence of mercuric oxide. The reaction may be carried out in an organic or an aqueous-organic solvent. Suitable organic solvents include alcohol, ether, aromatic hydrocarbons and dimethylformamide. Ethanol or aqueous ethanol is the preferred solvent. The reaction medium is heated, preferably to a temperature between about 25° C., and about 120° C., for at least about one-half hour, preferably for about one to about ten hours.

Compounds of the present invention may exist in anhydrous, hydrated, or partially hydrated forms. Anhydrous, hydrated, and partially hydrated forms are equivalent for the purpose of the present invention. Compounds of the present invention may also exist in solvated or partially solvated forms which are equivalent to the anhydrous form for the purposes of the present invention.

The non-toxic, pharmaceutically acceptable acid addition salts of the compounds of the invention are prepared by conventional reaction with equivalent amounts of organic or inorganic acids. Exemplary pharmaceutical salts include hydrochloric, hydrobromic, sulfuric, methanesulfonic and benzenesulphonic salts.

The antihypertensive action of the compounds of the invention was demonstrated by the following experiments. For testing, 18 week old rats of the Okamoto strain of spontaneously hypertensive animals are prepared surgically with a polyethylene cannula. The animals are dosed initially at 50 mg/kg by gastric gavage. Blood pressure and heart rate are then monitored for a 24 hour period. Further descriptions of this methodolgy may be found in A. Ebihara and B. L. Martz, Am. J. Med. Sci., 259: 257 (1970) and in R. Taber, et al., Clin. Pharm. Therap., 11: 269 (1970). These experiments are considered standard tests in mammals and are indicative of utility for treatment of similar disease states in humans.

When tested in this manner, the compounds of the invention exhibit oral antihypertensive activity. The results are set forth in the Table of Compounds below.

Some compounds of this invention have been observed to lower blood pressure in the spontaneously hypertensive rat (SHR) by as much as 30-35% within about 3-5 hours at a screening dose of about 50 mg/kg administered orally. Good activity for these compounds, about 20-25% blood pressure lowering in spontaneously hypersensitive rats, has been observed down to dosages of about 3 mg/kg. The antihypertensive effect has been maintained when dosing is administered chronically over a three day period. Some compounds of this invention have been shown to be well tolerated in the spontaneously hypertensive rats at dosages up to about 1000 mg/kg/day for about seven days.

able salts thereof together with a pharmaceutically acceptable, non-toxic carrier. The compositions of the present invention may be administered parenterally in combination with conventional injectable liquid carriers such as sterile pyrogen-free water, sterile peroxide-free ethyl oleate, dehydrated alcohols and propylene glycol. Suitable pharmaceutical adjuvants for the parenteral solutions include stabilizing agents, solubilizing agents, buffers and viscosity regulators. Some suitable adjuvants are ethanol, ethylene diamine tetraacetic acid, tartrate buffers, citrate buffers, and high molecular weight polyethylene oxide viscosity regulators. These pharmaceutical formulations may be injected intramuscularly, intraperitonealy, or intravenously.

The compositions of the present invention are preferably administered to mammals orally in combination

TABLE OF COMPOUNDS

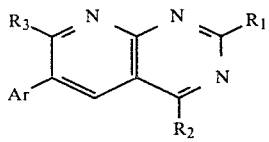

| Example | $R_1$ | $R_2$ | $R_3$ | Ar | Activity* | Method of Preparation | Melting Point °C. |
|---|---|---|---|---|---|---|---|
| 1 | $CH_3$ | H | $NH_2$ | 2,5-dichlorophenyl | +++ | A | 287-289** |
| 2 | $CH_3$ | H | $NH_2$ | 2-chlorophenyl | + | B | 259-260 |
| 3 | $CH_3$ | H | $NHOOCH_3$ | 2,6-dichlorophenyl | +++ | C | 202-203 |
| 4 | $CH_3$ | H | $NH_2$ | 2-bromo-6-chlorophenyl | ++ | A | 272-274 |
| 5 | $CH_3$ | H | $NH_2$ | 2-chloro-6-methylphenyl | ++ | A | 267-271 |
| 6 | H | $CH_3$ | $NH_2$ | 2,6-dichlorophenyl | ++ | A | 280-282 |
| 7 | $CH_3$ | $CH_3$ | $NH_2$ | 2,6-dichlorophenyl | +++ | A | 239-240 |
| 8 | $CH_3$ | H | NHCHO | 2,6-dichlorophenyl | ++ | D | 257-259 (dec.) |
| 9 | $CH_3$ | H | $NHOOCF_3$ | 2,6-dichlorophenyl | ++ | E | 195-199 (dec.) |
| 10 | $CH_3$ | H | NHCO-2-furyl | 2,6-dichlorophenyl | ++ | F | 228-230.5 |
| 11 | $CH_3$ | H | $NHCOCH_2Cl$ | 2,6-dichlorophenyl | ++(***) | G | >170° C.(dec.) |
| 12 | $CH_3$ | H | $NHCONHCH_3$ | 2,6-dichlorophenyl | + | H | 168-171 (dec.) |
| 13 | $CH_3$ | H | $NHCON(CH_3)_2$ | 2,6-dichlorophenyl | ++ | I | 177-181 |
| 14 | $CH_3$ | H | $NHSO_2CH_3$ | 2,6-dichlorophenyl | + | J | 212-213 |
| 15 | $CH_3$ | H | $NHC(S)NHCH_3$ | 2,6-dichlorophenyl | + | K | 207.5-208.5 |
| 16 | $CH_3$ | H | $N=CHN(CH_3)_2$ | 2,6-dichlorophenyl | ++ | L | 236-238 |
| 17 | $CH_3$ | H | $N=C(NHCH_3)NHCH_3$ | 2,6-dichlorophenyl | + | M | 279-283 |
| 18 | H | H | $NH_2$ | 2,6-dichlorophenyl | ++ | A | 328-330 |
| 19 | $CH_3$ | H | $NH_2$ | 2-methylphenyl | + | B | 234-235 |
| 20 | $CH_3$ | H | $NH_2$ | 2-bromophenyl | + | A | 228-230 |
| 21 | $CH_3$ | H | $NH_2$ | 2,4-dichlorophenyl | + | A | 259-161 |
| 22 | $CH_3$ | H | $NH_2$ | 2,4,6-trimethylphenyl | + | A | 254-255 |
| 23 | $CH_3$ | H | $NH_2$ | 2,6-dimethylphenyl | + | A | 273-275 |
| 24 | H | H | $NH_2$ | 2-methylphenyl | ++ | A | 253-255 |
| 25 | H | H | $NH_2$ | 2,6-dimethylphenyl | + | A | 285-287 |
| 26 | $CH_2CH_3$ | H | $NH_2$ | 2,6-dichlorophenyl | + | A | 269-270 |
| 27 | H | H | $NH_2$ | 2-ethylphenyl | ++ | A | 235-236.5 |
| 28 | H | H | $NH_2$ | 2-bromophenyl | + | A | 265-267 |
| 29 | H | H | $NH_2$ | 2-bromo-6-chlorophenyl | ++ | A | 326-330 |
| 30 | H | H | $NH_2$ | 2-iodophenyl | + | A | 262-264.5 |
| 31 | H | H | $NH_2$ | 2-chloro-6-methylphenyl | + | A | 300-302 |
| 32 | $CH_3$ | H | $NH_2$ | 2,6-dibromophenyl | ++ | B | 264-267 |
| 33 | H | H | $NHCOCH_3$ | 2,6-dichlorophenyl | + | C | 215-217 |
| 34 | $CH_3$ | H | $NHCOCH_2CH_3$ | 2,6-dichlorophenyl | +++ | C | 192-193 |
| 35 | $CH_3$ | H | NHCO-2-pyridyl | 2,6-dichlorophenyl | ++ | F | 260.5-262.5 |
| 36 | $CH_3$ | H | NHCO-3-pyridyl | 2,6-dichlorophenyl | ++ | F | 174.5-176 |
| 37 | $CH_3$ | H | $NHCOCH_2OCH_3$ | 2,6-dichlorophenyl | ++ | F | 185-189 |
| 38 | $CH_3$ | H | $NHCO_2CH_3$ | 2,6-dichlorophenyl | +++ | G | 136-139 (dec.) |
| 39 | $CH_3$ | H | NHCOphenyl | 2,6-dichlorophenyl | ++ | E | 185-187 |

*blood pressure lowering at 50 mg/kg SUR test
+ = 10-20%
++ = 20-30%
+++ = 30%
**methane sulfonate salt m.p. 142° C.
***blood pressure lowering at 10 mg/kg in SUR test The compounds of the invention or the non-toxic pharmaceutically acceptable salts thereof, may be administered to mammals in pharmaceutical formulations comprising an effective amount of the compounds of the invention or the non-toxic pharmaceutically acceptable salts thereof together with a pharmaceutically acceptable, non-toxic carrier.

with conventionally compatible carriers in solid or in liquid form. These oral compositions may contain conventional ingredients such as binding agents like syrups, acacia, gelatin, sorbitol, tragacanth and polyvinylpyrrolidone. These oral compositions may also include fillers such as lactose, mannitols, starch, calcium phosphate, sorbitol or methylcellulose. These compositions may additionally contain lubricants such as magnesium stearate, high-molecular weight polymers such as polyethylene glycol, high-molecular weight fatty acids (stearic acid) or silica, disintegrants such as starch, and wetting agents such as sodium lauryl sulfate.

The oral compositions may take any convenient form such as tablets, capsules, lozenges, aqueous or oily suspensions, emulsions, or even dry products which may be reconstituted with water or other liquid medium before use. The solid or liquid oral forms may contain flavors, sweeteners, and preservatives such as alkyl p-hydroxybenzoates. The liquid forms may contain suspending agents such as sorbitol, glucose or other sugar syrups, methylcelluslose or carboxymethylcellulose, and gelatin, and may contain emulsifying agents such as lecithin or sorbitan monooleate, and conventional thickening agents. The liquid composition may optionally be encapsulated in capsules, for example gelatin capsules.

The dosage levels of the compositions of the present invention will depend on the nature and severity of the biological ailment to be treated, as well as on the path of administration. The compositions of the present invention may be administered in dosages generally from about 1 mg/kg to about 250 mg/kg, typically from about 2 mg/kg to about 50 mg/kg and most typically from about 10 mg/kg to about 50 mg/kg. The age, weight, and health of the patient will have to be taken into account when determining optimum dosage levels to be administered.

The invention is illustrated by the following non-limiting Examples.

The Examples below illustrate in detail the preparation of some of the specific compounds in the Table of Compounds employing the general methods described above. The preparation of other specific compounds in the Table of Compounds is determined by reference to the column headed Method of Preparation. The letter designations in said column correspond to the letter designations of the detailed Examples.

EXAMPLE 1

Method A 6-(2,6-Dichlorophenyl)-2-methylpyrido[2,3,-d]-pyrimidin-7-amine

A mixture of 76.5 g of 4-amino-2-methylpyrimidine-5-carbonitrile, 380 ml of 97% formic acid, 380 ml of water, and 8 g of Raney nickel catalyst is treated in a Parr pressure apparatus with hydrogen gas at an initial pressure of 51 psi at room temperature for 2.75 hours. The catalyst is removed by filtration and the filtrate is treated with 47.5 ml of concentrated hydrochloric acid and evaporated at reduced pressure. The residue is dissolved in hot water, treated with charcoal and filtered. Neutralization of the filtrate with concentrated ammonium hydroxide precipitates the product which is then collected by filtration and washed with water. Recrystallization from ethanol gives 37.9 g of 4-amino-2-methylpyrimidine-5-carboxaldehyde, mp 191°–192.5° C.

2,6-Dichlorophenylacetonitrile 8.1 g and 4-amino-2-methylpyrimidine-5-carboxaldehyde 6.9 g is added to a solution of 0.4 g of sodium metal in 60 ml of anhydrous ethanol. This mixture is heated at reflux for 3 hours. Upon cooling, the crude product precipitates and is collected by filtration. The solid is recrystallized from ethanol, with charcoal treatment, to give 5.5 g of 6-(2,6-dichlorophenyl)-2-methylpyrido[2,3-d]pyrimidin-7-amine, mp 287°–289° C., which may occlude varying amounts of water, depending on the drying conditions.

A solution of 5.0 g of the free base described above in 150 ml of isopropanol is treated with 5 ml of methanesulfonic acid. The precipitate, formed by diluting the mixture with 900 ml of ether, is filtered and recrystallized from an ethanol/ether mixture to give 1.9 g of the salt, mp 142° C. with decomposition, which is hydrated and contains a formula weight of methanesulfonic acid.

6-(2,6-Dichlorophenyl)-2-methylpyrido[2,3-d]-pyrimidin-7-amine has been shown to lower blood pressure in spontaneously hypertensive rats (SHR) by over 30% within 3–5 hours at the screening dose of 50 mg/kg orally, with good activity (20–25% blood pressure lowering) down to a dose of 3 mg/kg. The effect is maintained when dosing is done chronically over a three day period. The compound appears to be well tolerated in rats at 1000 mg/kg/day orally for seven days.

EXAMPLE 2

Method B 6-(2-Chlorophenyl)-2-methylpyrido[2,3-d]pyrimidin-7-amine

2-Chlorophenylacetonitrile 4.0 g and 4-amino-2-methylpyrimidine-5-carboxaldehyde 3.6 g are added to a solution prepared by dissolving 0.2 g of sodium metal in 40 ml of 2-ethoxy-ethanol. The mixture is heated at reflux for 2 hours, and then cooled. The crude product precipitates as a solid and is collected by filtration. After recrystallization from aqueous dimethylformamide, 3.4 g of 6-(2-chlorophenyl)-2-methylpyrido[2,3-d]pyrimidin-7-amine, mp 259°–260° C. is obtained.

EXAMPLE 3

Method C

N-[6-(2,6-dichlorophenyl)-2-methylpyrido[2,3-d]-pyrimidin-7-yl]acetamide 6-(2,6-Dichlorophenyl)-2-methylpyrido[2,3-d]-pyrimidin-7-amine is added to about 50 ml of acetic anhydride and the mixture is then heated on a steam bath for about 30 minutes. The mixture is added to water and warmed to decompose excess acetic anhydride. The product is isolated by extracting the mixture with choloroform, drying the organic layer and concentrating the latter to dryness. Trituration with ether yields a solid material, which is then recrystallized from ethyl acetate, yielding 1.9 g of N-[6-(2-6-dichlorophenyl)-2-methylpyrido[2,3-d]pyrimidin-7-yl]acetamide, mp 202°–203° C.

N-[6-(2,6-dichlorophenyl)-2-methylpyrido[2,3-d]-pyrimidin-7-yl]acetamide has been demonstrated to lower blood pressure in spontaneously hypertensive rats by over 30% at dosage of about 50 mg/kg.

EXAMPLE 4

6-(2-Bromo-6-chlorophenyl)-2-methylpyrido[2,3-d]-pyrimidin-7-amine

A mixture of 20.0 g of 2-bromo-6-chlorotoluene [J. B. Cohen and M. S. Raper, J. Chem. Soc., 85: 1268 (1904)] and 18.0 g of N-bromosuccinimide in 200 ml of carbon tetrachloride is heated to reflux in the presence of 10 mg. of benzoyl peroxide as catalyst. After 24 hours, the mixture is cooled and filtered, and the filtrate is concentrated to dryness to give a lachrymatory oil which solidifies on standing, mp 56°–60° C. Spectral data confirms that this crude product is primarily 6-chloro-alpha,2-dibromotoluene which is used in the subsequent reaction without further purification.

A solution of 31.3 g of the crude 6-chloro-alpha,2-dibromotoluene in 100 ml of warm ethanol is treated with a solution of 6.7 g of potassium cyanide in 10 ml of water and the mixture is heated at reflux for 4 hours. The crude product is isolated by pouring the cooled reaction mixture into water and filtering the resulting precipitate. Recrystallization of this solid from aqueous ethanol then gives 12.4 g of 2-bromo-6-chlorophenylacetonitrile, mp 82°–84° C.

Following the procedure for Example 1, 2-bromo-6-chlorophenylacetonitrile is condensed with 4-amino-2-methylpyrimidin-5-carboxaldehyde to give 6-(2-bromo-6-chlorophenyl)-2-methylpyrido[2,3-d]-pyrimidin-7-amine, mp 272°–274° C., after recrystallization from acetonitrile.

EXAMPLE 5

6-(2-Chloro-6-methylphenyl)-2-methylpyrido[2,3-d]-pyrimidin-7-amine

A solution of 24 g of 2-chloro-6-methylbenzaldehyde [L. G. Humber, J. Med. Chem., 7, 826 (1964)] in 200 ml of methanol is cooled in an ice bath while 6.0 g of sodium borohydride is added in portions. After stirring overnight at room temperature, the mixture is concentrated to dryness and the residue is partitioned between water and ether. The organic layer is washed with dilute hydrochloric acid, dried, and concentrated to yield the crude product. Recrystallization from benzene/hexane gives 20.8 g of 2-chloro-6-methylbenzyl alcohol, mp 83°–86° C. in two crops.

The 2-chloro-6-methylbenzyl alcohol is dissolved in 100 ml of benzene, treated with 25 ml of thionyl chloride and the mixture is heated at reflux for 3 hours. Concentration of this mixture to dryness leaves a liquid which partly solidifies. The product containing liquid is decanted from the solid by-product and distilled to yield 7.8 g of alpha,2-dichloro-6-methyltoluene as a colorless liquid with bp. 118°–122° C./17–18 mm of Hg.

A solution of 9.4 g of alpha,2-dichloro-6-methyltoluene in 30 ml of 95% ethanol is treated with a solution of 3.8 g of potassium cyanide in 5 ml of water and heated at reflux for 6 hours. The crude product is isolated by pouring the cooled reaction mixture into water and filtering the precipitated solid. Recrystallization from aqueous ethanol gives 4.9 g of pure 2-chloro-6-methylphenylacetonitrile, mp 49°–51° C., in two crops.

Following the procedure of Example 1, 2-chloro-6-methylphenylacetonitrile is condensed with 4-amino-2-methylpyrimidine-5-carboxaldehyde to give 6-(2-chloro-6-methylphenyl)-2-methylpyrido[2,3-d]-pyrimidin-7-amine, mp 267°–271° C., after recrystallization from isopropanol.

EXAMPLE 6

6-(2,6-Dichlorophenyl)-4-methylpyrido[2,3-d]-pyrimidin-7-amine

Following the procedure of Example 1, 4-amino-6-methylpyrimidine-5-carbonitrile is hydrogenated to give 4-amino-6-methylpyrimidine-5-carboxaldehyde, mp 158°–160° C., after recrystallization from ethanol.

4-Amino-6-methylpyrimidine-5-carboxaldehyde is then condensed with 2,6-dichlorophenylacetonitrile. The crude product is isolated by concentrating the reaction mixture to dryness and partitioning the residue between chloroform and water. Drying and concentration of the organic layer gives a residue which is chromatographed on silica gel. The product is eluted with 1/99 mixture of methanol/chloroform and recrystallized from ethanol to give pure 6-(2,6-dichlorophenyl)-4-methylpyrido[2,3-d]pyrimidin-7-amine, mp 280°–282° C.

EXAMPLE 7

6-(2,6-Dichlorophenyl)-2,4-dimethylpyrido[2,3-d]-pyrimidin-7-amine

Following the procedure of Example 1, 4-amino-2,6-dimethylpyrimidin-5-carbonitrile is reduced to give 4-amino-2,6-dimethylpyrimidine-5-carboxaldehyde, mp 148°–156° C., after recrystallization from ethanol.

4-Amino-2,6-dimethylpyrimidine-5-carboxaldehyde is then condensed with 2,6-dichlorophenylacetonitrile. The product is isolated and purified in the manner described in Example 6, yielding 6-(2,6-dichlorophenyl)-2,4-dimethylpyrido[2,3-d]pyrimidin-7-amine, mp 239°–240° C., after recrystallization from ethyl acetate.

EXAMPLE 8

Method D

N-[6-(2,6-Dichlorophenyl)-2-methylpyrido[2,3-d]pyrimidin-7-yl]formamide

A solution of formic acetic anhydride is prepared by adding 6.2 g of 98% formic acid to 13.4 of acetic anhydride cooled to 0° C. This mixture is then warmed at 45°–50° C. for 15 minutes. After cooling the solution at 0° C., 10.0 g of 6-(2,6-dichlorophenyl)-2-methylpyrido[2,3-d]pyrimidin-7-amine is added, then 15 ml of dry ethyl ether is added to the solution. The resulting suspension is stirred for 2 hours at room temperature, until a clear solution is obtained. The solution is then concentrated to dryness at reduced pressure and the residue is triturated with ether and filtered. After recrystallization from ethanol, 2.9 g of N-[6-(2,6-dichlorophenyl)-2-methylpyrido[2,3-d]pyrimidin-7-yl]formamide, mp 257°–259° C. (dec.), is obtained.

EXAMPLE 9

Method E

N-[6-(2,6-dichlorophenyl)-2-methylpyrido[2,3-d]pyrimidin-7-yl]-2,2,2-trifluoroacetamide 6-(2,6-Dichlorophenyl)-2-methylpyrido[2,3-d]-pyrimidin-7-amine, 10 g, is added to a solution of 10 ml of trifluoroacetic anhydride in 10 ml of trifluoroacetic acid. This mixture is stirred for 18 hours at room temperature. The resulting solution is concentrated to dryness at reduced pressure. The residue is dissolved in chloroform and this solution is washed with aqueous sodium bicarbonate solution until it is neutral. The organic layer is dried over magnesium sulfate, filtered, and concentrated to dryness to yield the crude product. This is purified by successive recrystallizations from acetonitrile, ethyl acetate and toluene to yield 2.0 g of N-[6-(2,6-dichlorophenyl)-2-methylpyrido[2,3-d]pyrimidin-7-yl]-2,2,2-trifluoroacetamide, mp 195°–199° C. (dec.).

EXAMPLE 10

Method F

N-[6-(2,6-dichlorophenyl)-2-methylpyrido[2,3-d]-pyrimidin-7-yl]-2-furancarboxamide A suspension of 3.0 g of 6-(2,6-dichlorophenyl)-2-methylpyrido[2,3-d]pyrimidin-7-amine and 1.8 g of 2-furoic acid in 50 ml of chloroform is boiled on a steam bath until the distilling vapors reach a temperature of 61° C. The mixture is cooled to about 40° C. and 2.6 g of carbonyldiimidazole is added cautiously. Gas is evolved. When gas evolution has ceased, the resulting solution is heated at reflux for 30 hours. The cooled reaction mixture is chromatographed directly on a column of 150 g of silica gel. The crude product is eluted with a 99/1 chloroform/methanol mixture. This is purified by trituration with ether and recrystallization of the resulting solid from a chloroform/ether mixture. N-[6-(2,6-dichlorophenyl)-2-methylpyrido[2,3-d]pyrimidin-7-yl]-2-furancarboxamide is obtained as yellow crystals, mp 228°–230.5° C.

EXAMPLE 11

Method G

2-Chloro-N-[5-(2,6-dichlorophenyl)-2-methylpyrido-[2,3-d]pyrimidin-7-yl]acetamide A suspension of 3.0 g of 6-(2,6-dichlorophenyl)-2-methylpyrido[2,3-d]pyrimidin-7-amine and 50 ml of 1,2-dichloroethane is boiled on a steam bath until the distilling vapors reach a temperature of 83° C. The suspension is cooled to room temperature and 1.6 g of chloroacetic acid and 2.6 g of carbonyldiimidazole are added sequentially. The mixture is stirred at room temperature for 3 hours and the resulting solution is immediately chromatographed over 150 g of silica gel. The crude product is eluted with a 99/1 chloroform/methanol mixture. Trituration of this with ether gives pure 2-chloro-N-[6-(2,6-dichlorophenyl)-2-methyl-pyrido[2,3-d]-pyrimidin-7-yl]acetamide, decomposing above ca 170° C.

EXAMPLE 12

Method H

N-[6-(2,6-dichlorophenyl)-2-methylpyrido[2,3-d]-pyrimidin-7-yl]-N'-methylurea

A slurry of 3.0 g of 6-(2,6-dichlorophenyl)-2-methylpyrido[2,3-d]-pyrimidin-7-amine in 20 ml of methyl isocyanate is heated at reflux for 3 hours to obtain a yellow solution. This is stirred overnight at room temperature and diluted with 20 ml of ether. The solvent and excess isocyanate are evaporated and the solid residue of crude product is purified by recrystallization from ethyl acetate to give N-[6-(2,6-dichlorophenyl)-2-methylpyrido[2,3-d]-pyrimidin-7-yl]-N'-methylurea, mp 168°–171° C. (dec.).

EXAMPLE 13

Method I

N-[6-(2,6-dichlorophenyl)-2-methylpyrido[2,3-d]-pyrimidin-7-yl]-N',N'-dimethylurea Following the procedure of Example 11, 3.0 g of 6-(2,6-dichlorophenyl)-2-methylpyrido[2,3-d]pyrimidin-7-amine and 2.0 g of carbonyldiimidazole are reacted at reflux in 50 ml of 1,2-dichloroethane for 24 hours. The mixture is cooled, treated sequentially with 1.5 g of dimethylamine hydrochloride and 2 ml of triethylamine, and stirred at room temperature for 1.5 hours. It is then washed with water prior to chromatography over 150 g of silica gel. The product is eluted with a 99/1 chloroform/methanol mixture and recrystallized from ethyl acetate to give N-[6-(2,6-dichlorophenyl)-2-methylpyrido[2,3-d]pyrimidin-7-yl]-N',N'-dimethylurea, mp 177°–181° C.

EXAMPLE 14

Method J

N-[6-(2,6-dichlorophenyl)-2-methylpyrido[2,3-d]-pyrimidin-7-yl]methanesulfonamide A stirred suspension of 3.0 g of 6-(2,6-dichlorophenyl)pyrido[2,3-d]pyrimidin-7-amine in 100 ml of dry 1,2-dichloroethane is cooled to 0° C. and treated with 1.2 g of methanesulfonyl chloride followed by dropwise addition of 1.0 g of triethylamine. Stirring is continued while the mixture is allowed to warm to room temperature during 4 hours. If the reaction is not complete as judged by thin layer chromatography on silica gel, the reaction mixture is cooled to 0° C. and treated with an additional 1.2 g of methanesulfonyl chloride followed by 1.0 g of triethylamine. The mixture is stirred overnight at room temperature, filtered from insoluble material and chromatographed on 150 g of silica gel to separate the crude product. Recrystallization from toluene gives pure N-[6-(2,6-dichlorophenyl)-2-methylpyrido[2,3-d]pyrimidin-7-yl]methanesulfonamide, mp 212°–213° C.

EXAMPLE 15

Method K

N-[6-(2,6-dichlorophenyl)-2-methylpyrido[2,3-d]-pyrimidin-7-yl]-N'-methylthiourea A mixture of 25.0 g of 6-(2,6-dichlorophenyl)-2-methylpyrido[2,3-d]pyrimidin-7-amine and 18.0 g of methyl isothiocyanate in 125 ml of toluene is heated at reflux for 28 hours. Cooling gives a precipitate of crude product which is collected by filtration and washed with ether. Further purification may be effected by recrystallization from isopropanol to give N-[6-(2,6-dichlorophenyl)-2-methylpyrido[2,3-d]-pyrimidin-7-yl]-N'-methylthiourea, mp 207.5°–208.5° C. (dec.).

EXAMPLE 16

Method L

N'-[6-(2,6-dichlorophenyl)-2-methylpyrido[2,3-d]-pyrimidin-7-yl]-N,N-dimethylmethanimidamide A mixture of 2.1 g of 6-(2,6-dichlorophenyl)-2-methylpyrido[2,3-d]pyrimidin-7-amine in 10 ml of dimethylformamide dimethyl acetal is warmed on a steam bath. Solution occurs followed by an exothermic reaction and precipitation of a solid. This mixture is stirred at room temperature for 16 hours and then diluted with ether and filtered to obtain the crude product as a yellow solid. Recrystallization of this from acetonitrile gives pure N'-[6-(2,6-dichlorophenyl)-2-methylpyrido[2,3-d]pyrimidin-7-yl]-N,N-dimethylmethanimidamide, mp 236°–238° C.

EXAMPLE 17

Method M

N-[6-(2,6-dichlorophenyl)-2-methylpyrido[2,3-d]-pyrimidin-7-yl]-N'-N''-dimethylguanidine A mixture of 3.8 g of N-[6-(2,6-dichlorophenyl)-2-methylpyrido[2,3-d]pyrimidin-7-yl]-N'-methylthiourea, 2.2 g of yellow mercuric oxide, 4 ml of a 40% aqueous solution of methylamine and 40 ml of 95% ethanol is warmed to reflux during 15 minutes. The hot mixture is filtered from the black precipitate of mercuric sulfide and the filtrate is concentrated to yield the crude product as a yellow solid. Recrystallization from 50% aqueous ethanol gives pure N-[6-(2,6-dichlorophenyl)-2-methylrido[2,3-d]pyrimidin-7-yl]-N',N''-dimethylguanidine, mp 279°-283° C.

We claim:

1. A compound having the formula

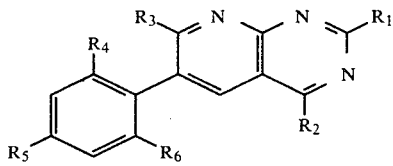

and pharmaceutically acceptable acid addition salts thereof; where $R_1$ and $R_2$ are hydrogen or alkyl; $R_4$ is halogen or alkyl; $R_5$ and $R_6$ are hydrogen, halogen, or alkyl; $R_3$ is

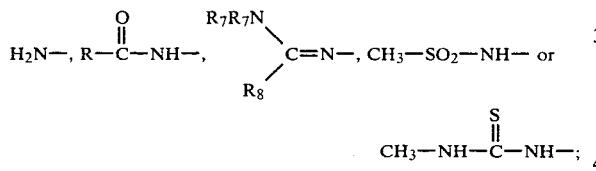

R is hydrogen, alkyl, haloalkyl, alkoxy, alkoxymethylene, mono- and dialkylamino, trifluoromethyl, furyl, pyridyl, or phenyl; $R_7$ is hydrogen or alkyl; $R_8$ is hydrogen or alkylamino; wherein alkyl and alkoxy have 1 to 3 carbon atoms; with the provisos that when $R_3$ is $NH_2$; $R_2$, $R_5$ and $R_6$ are hydrogen and (a) $R_1$ is hydrogen, $R_4$ is not chlorine; (b) $R_1$ is methyl, $R_4$ is not fluoro, iodo or ethyl; (c) $R_1$ is ethyl, $R_4$ is not chloro or methyl; when $R_8$ is hydrogen, $R_7$ is not hydrogen.

2. A compound having the formula

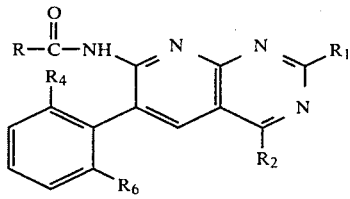

and non-toxic pharmaceutically acceptable acid addition salts thereof; where $R_1$ and $R_2$ are hydrogen or methyl; $R_4$ is halogen, methyl or ethyl; $R_6$ is hydrogen, chlorine, bromine or methyl; R is hydrogen, methyl, ethyl, chloromethyl, methoxy, methoxymethylene, methyl- and dimethylamino, trifluoromethyl, 2-furyl, 2- and 3-pyridyl or phenyl.

3. A compound according to claim 1 having the formula

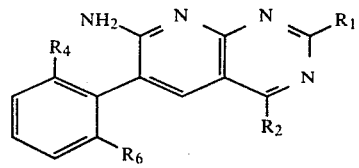

and non-toxic pharmaceutically acceptable acid addition salts thereof; where $R_1$ and $R_2$ are hydrogen or methyl; $R_4$ is halogen, methyl or ethyl; $R_6$ is hydrogen, chlorine, bromine or methyl; with the provisos that when $R_2$ and $R_6$ are hydrogen and (a) $R_1$ is hydrogen, $R_4$ is not chlorine; (b) $R_1$ is methyl, $R_4$ is not fluoro, iodo or ethyl; (c) $R_1$ is ethyl, $R_4$ is not chloro or methyl.

4. The compound of claim 3 which is 6-(2,6-dichlorophenyl)-2-methylpyrido[2,3-d]pyrimidin-7-amine.

5. The compound of claim 3 which is 6-(2,6-dichlorophenyl)pyrido[2,3-d]pyrimidin-7-amine.

6. The compound of claim 3 which is 6-(2-methylphenyl)pyrido[2,3-d]pyrimidin-7-amine.

7. The compound of claim 2 which is N-[6-(2,6-dichlorophenyl)-2-methylpyrido[2,3-d]pyrimidin-7-yl]-acetamide.

8. The compound of claim 3 which is 6-(2-bromo-6-chlorophenyl)-2-methylpyrido[2,3-d]pyrimidin-7-amine.

9. The compound of claim 3 which is 6-(2-bromo-6-chlorophenyl)pyrido[2,3-d]pyrimidin-7-amine.

10. The compound of claim 3 which is 6-(2,6-dichlorophenyl)-4-methylpyrido[2,3-d]pyrimidin-7-amine.

11. The compound of claim 3 which is 6-(2,6-dichlorophenyl)-2,4-dimethylpyrido[2,3-d]pyrimidin-7-amine.

12. The compound of claim 3 which is 6-(2,6-dibromophenyl)-2-methylpyrido[2,3-d]pyrimidin-7-amine.

13. The compound of claim 2 which is N-[6-(2,6-dichlorophenyl)-2-methylpyrido[2,3-d]pyrimidin-7-yl]-propanamide.

14. The compound of claim 2 which is N-[6-(2,6-dichlorophenyl)-2-methylpyrido[2,3-d]pyrimidin-7-yl]-2-furancarboxamide.

15. The compound of claim 2 which is N-[6-(2,6-dichlorophenyl)-2-methylpyrido[2,3-d]pyrimidin-7-yl]-2-pyridinecarboxamide.

16. The compound of claim 2 which is N-[6-(2,6-dichlorophenyl)-2-methylpyrido[2,3-d]pyrimidin-7-yl]-3-pyridinecarboxamide.

17. The compound of claim 2 which is N-[6-(2,6-dichlorophenyl)-2-methylpyrido[2,3-d]pyrimidin-7-yl]-2-methoxyacetamide.

18. The compound of claim 2 which is 2-chloro-N-[6-(2,6-dichlorophenyl)-2-methylpyrido[2,3-d]pyrimidin-7-yl]acetamide.

19. The compound of claim 2 which is [6-(2,6-dichlorophenyl)-2-methylpyrido[2,3-d]pyrimidin-7-yl]-carbamic acid methyl ester.

20. The compound of claim 2 which is N-[6-(2,6-dichlorophenyl)-2-methylpyrido[2,3-d]pyrimidin-7-yl]-benzamide.

21. A pharmaceutical composition for treating hypertension in mammals comprising an effective amount of a compound having the formula:

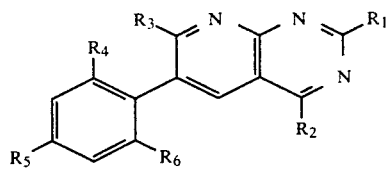

or a pharmaceutically acceptable acid addition salt thereof; where $R_1$ and $R_2$ are hydrogen or alkyl; $R_4$ is halogen or alkyl; $R_5$ and $R_6$ are hydrogen, halogen or alkyl; $R_3$ is

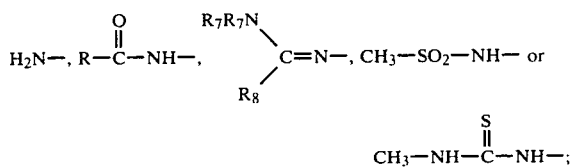

R is hydrogen, alkyl, haloalkyl, alkoxy, alkoxymethylene, mono- and dialkylamino, trifluoromethyl, furyl, pyridyl or phenyl; $R_7$ is hydrogen or alkyl; and $R_8$ is hydrogen or alkylamino; wherein alkyl and alkoxy have 1 to 3 carbon atoms; with the privisos that when $R_3$ is $NH_2$; $R_2$, $R_5$ and $R_6$ are hydrogen and (a) $R_1$ is hydrogen, $R_4$ is not chlorine; (b) $R_1$ is methyl, $R_4$ is not fluoro, iodo or ethyl; (c) $R_1$ is ethyl, $R_4$ is not chloro or methyl; when $R_8$ is hydrogen, $R_7$ is not hydrogen.

22. A pharmaceutical composition for treating hypertension in mammals comprising an effective amount of a compound having the formula

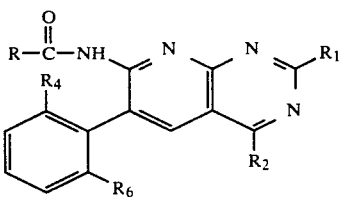

or a pharmaceutically acceptable acid addition salt thereof; where $R_1$ and $R_2$ are hydrogen or methyl; $R_4$ is halogen, methyl or ethyl; $R_6$ is hydrogen, chlorine, bromine or methyl; and R is hydrogen, methyl, ethyl, chloromethyl, methoxy, methoxymethylene, methyl- and dimethylamino, trifluoromethyl, 2-furyl, 2- and 3-pyridyl or phenyl.

23. A method of treating hypertension in mammals comprising the administration of an effective amount of the compound having the structure:

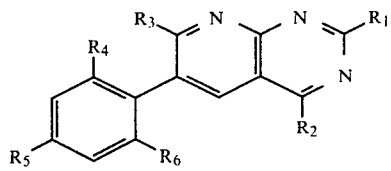

or a pharmaceutically acceptable acid addition salt thereof; where $R_1$ and $R_2$ are hydrogen or alkyl; $R_4$ is halogen or alkyl; $R_5$ and $R_6$ are hydrogen, halogen, or alkyl; $R_3$ is

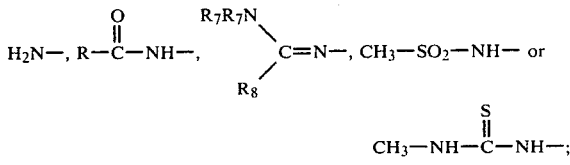

R is hydrogen, alkyl, haloalkyl, alkoxy, alkoxymethylene, mono- and dialkylamino, trifluoromethyl, furyl, pyridyl or phenyl; $R_7$ is hydrogen or alkyl; and $R_8$ is hydrogen, or alkylamino; wherein alkyl and alkoxy have 1 to 3 carbon atoms; with the provisos that when $R_3$ is $NH_2$; $R_2$, $R_5$ and $R_6$ are hydrogen and
 (a) $R_1$ is hydrogen, $R_4$ is not chlorine
 (b) $R_1$ is methyl, $R_4$ is not fluoro, iodo or ethyl,
 (c) $R_1$ is ethyl, $R_4$ is not chloro or methyl; when $R_8$ is hydrogen, $R_7$ is not hydrogen.

24. A method of treating hypertension in mammals comprising the administration of an effective amount of a compound having the formula

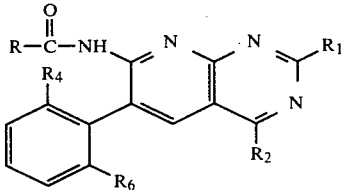

or a pharmaceutically acceptable acid addition salt thereof; where $R_1$ is hydrogen or methyl; $R_4$ is halogen, methyl or ethyl; $R_6$ is hydrogen, chlorine, bromine, or methyl; R is hydrogen, methyl, ethyl, chloromethyl, methoxy, methoxymethylene, methyl- and dimethylamino, trifluoromethyl, 2-furyl, 2- and 3-pyridyl or phenyl.

* * * * *